(12) United States Patent
Lavedan et al.

(10) Patent No.: US 9,057,104 B2
(45) Date of Patent: Jun. 16, 2015

(54) ANTIPSYCHOTIC TREATMENT BASED ON DRD2 OR ANKK1 SNP GENOTYPE

(75) Inventors: Christian Lavedan, Potomac, MD (US); Simona Volpi, Derwood, MD (US)

(73) Assignee: Vanda Pharmaceuticals, Inc., Washington, DC (US)

( * ) Notice: Subject to any disclaimer, the term of this patent is extended or adjusted under 35 U.S.C. 154(b) by 452 days.

(21) Appl. No.: 13/319,430

(22) PCT Filed: May 15, 2010

(86) PCT No.: PCT/US2010/035045
§ 371 (c)(1),
(2), (4) Date: Nov. 8, 2011

(87) PCT Pub. No.: WO2010/132866
PCT Pub. Date: Nov. 18, 2010

(65) Prior Publication Data
US 2012/0053207 A1    Mar. 1, 2012

Related U.S. Application Data

(60) Provisional application No. 61/178,934, filed on May 15, 2009.

(51) Int. Cl.
*C12Q 1/68*    (2006.01)

(52) U.S. Cl.
CPC ........ *C12Q 1/6883* (2013.01); *C12Q 2600/156* (2013.01); *C12Q 2600/106* (2013.01)

(58) Field of Classification Search
None
See application file for complete search history.

(56) References Cited

FOREIGN PATENT DOCUMENTS

| WO | 03054226 A2 | 7/2003 |
|---|---|---|
| WO | 03054226 A3 | 4/2004 |
| WO | 2005007871 A2 | 1/2005 |
| WO | 2005007871 A3 | 9/2005 |
| WO | 2006039663 A2 | 4/2006 |
| WO | 2006039663 A3 | 11/2006 |
| WO | 2008144599 A2 | 11/2008 |
| WO | 2008144599 A3 | 1/2009 |
| WO | 2009036056 A1 | 3/2009 |

OTHER PUBLICATIONS

Parsons et al; Psychiatric Genetics, vol. 17, 2007, pp. 159-163.*
Patent Cooperation Treaty, PCT Notification of Transmittal of the International Search Report and the Written Opinion of the International Searching Authority, or the Declaration for PCT/US2010/035045 dated Nov. 3, 2010, 24 pages.
Kondo et al., "Combination of dopamine D2 receptor gene polymorphisms as a possible predictor of treatment-resistance to dopamine antagonists in schizophrenic patients," Sep. 2003, pp. 921-926, Progress in Neuro-Psychopharmacology & Biological Psychiatry, vol. 27, No. 6 (XP002483913).
Lavedan et al., "Association of the NPAS3 gene and five other loci with response to the antipsychotic iloperidone identified in a whole genome association study," Jun. 2008, pp. 804-819, Molecular Psychiatry, vol. 14, No. 8 (XP002597954).
Lavedan et al., "Effect of a ciliary neurotrophic factor polymorphism on schizophrenia symptom improvement in an iloperidone clinical trial," Mar. 2008, pp. 289-301, Pharmacogenomics, vol. 9, No. 3 (XP009104913).
Young et al., "Prolactin levels in antipsychotic treatment of patients with schizophrenia carrying the DRD2*A1 allele," Aug. 2004, pp. 147-151, British Journal of Psychiatry, vol. 185 (XP002483915).
Patent Cooperation Treaty, PCT Notification Concerning Transmittal of International Preliminary Report on Patentability (Chapter 1 of the Patent Cooperation Treaty) for PCT/US2010/035045 dated Nov. 24, 2011, 14 pages.
Hamilton et al., "Association of the NPAS3 gene and five other loci with response to the antipsychotic iloperidone identified in a whole genome association study," 2009, pp. 804-819, Molecular Psychiatry, vol. 14.
Yasui-Furukori et al., "Association between dopamine-related polymorphisms and plasma concentrations of prolactin during risperidone treatment in schizophrenic patients," 2008, pp. 1491-1495, Progress in Neuro-Psychopharmacology & Biological Psychiatry, vol. 32.
Kwon et al., "Taq1A polymorphism in the dopamine D2 receptor gene as a predictor of clinical response to aripiprazole," 2008, pp. 897-907, European Neuropsychopharmacology, vol. 18.
Schafer et al., "Association of Short-Term Response to Haloperidol Treatment with a Polymorphism in the Dopamine D2 Receptor Gene," 2001, pp. 802-804, New York State Library, AJP in Advance.
Suzuki et al., "The relationship between dopamine D2 receptor polymorphism at the Taq1 A locus and therapeutic response to nemonapride, a selective dopamine antagonist, in schizophrenic patients," Pharmacogenetics. 10 (4):335-41 (2000).

* cited by examiner

*Primary Examiner* — Jehanne Sitton
(74) *Attorney, Agent, or Firm* — Hoffman Warnick LLC

(57) ABSTRACT

The present invention relates to the treatment of an individual with an antipsychotic based on individual's genotype at one or more single nucleotide polymorphism (SNP) associated with the dopamine receptor D2 (DRD2) and/or ankyrin repeat and kinase domain containing 1 (ANKK1) genes.

14 Claims, 4 Drawing Sheets

Vertical bars represent exons. The solid black bar shows the alternatively spliced exon 6 of DRD2. The broken arrows show the location of SNPs previously typed in a whole genome association study. The black solid arrows point to the locations of the SNPs analyzed in the study presented here. rs1800497 originally assigned to DRD2 was later shown to be located within ANKK1.

ANTIPSYCHOTIC TREATMENT BASED ON DRD2 OR ANKK1 SNP GENOTYPE

CROSS-REFERENCE TO RELATED APPLICATIONS

This application claims the benefit of U.S. Provisional Patent Application No. 61/178,934, filed 15 May 2009, which is hereby incorporated herein.

BACKGROUND OF THE INVENTION

Schizophrenia affects approximately 1% of the population. It is characterized by the presence of positive symptoms (unusual thoughts or perceptions, including hallucinations and delusions), negative symptoms (social withdrawal, lack of pleasure in everyday life), and impaired cognitive functions (verbal memory, information processing). Such symptoms may be indicative of other disorders, such as, for example, bipolar disorder.

A number of antipsychotic drugs have been approved to treat schizophrenia. However, patient response to treatment remains highly variable, and the discontinuation rate with antipsychotic treatment is high. No single antipsychotic agent offers optimal effect for every patient with schizophrenia. Few data are available to guide clinicians and patients in the selection of the most appropriate medication and in the improvement of treatment specificity for an individual patient. Pharmacogenomics provides the opportunity to discover genetic markers predictive of response. Knowing how a patient with schizophrenia might respond to a particular therapy based on his or her genetic makeup may enable clinicians to select the most optimal drug and dosage with less trial and error.

SUMMARY OF THE INVENTION

The present invention relates to the treatment of an individual with an antipsychotic based on individual's genotype at one or more single nucleotide polymorphism (SNP) associated with the dopamine receptor D2 (DRD2) and/or ankyrin repeat and kinase domain containing 1 (ANKK1) genes, as well as prediction of the efficacy of treating with an antipsychotic an individual having one or more SNP genotypes associated with relatively greater antipsychotic treatment efficacy.

One aspect of the invention provides a method of predicting the efficacy of using iloperidone in the treatment of at least one psychotic symptom in an individual, the method comprising: determining the individual's genotype at the rs1800497 single nucleotide polymorphism (SNP); and in the case that the individual's genotype at the rs1800497 SNP locus is associated with relatively greater iloperidone efficacy, predicting that treating the individual with iloperidone will be efficacious.

Another aspect of the invention provides a method of predicting the efficacy of using iloperidone in the treatment of at least one psychotic symptom in an individual, the method comprising: determining the individual's genotype at the rs2283265 single nucleotide polymorphism (SNP); and in the case that the individual's genotype at the rs2283265 SNP locus is associated with relatively greater iloperidone efficacy, predicting that treating the individual with iloperidone will be efficacious.

Still another aspect of the invention provides a method of predicting the efficacy of using iloperidone in the treatment of at least one psychotic symptom in an individual, the method comprising: determining the individual's genotype at the rs1076560 single nucleotide polymorphism (SNP); and in the case that the individual's genotype at the rs1076560 SNP locus is associated with relatively greater iloperidone efficacy, predicting that treating the individual with iloperidone will be efficacious.

Yet another aspect of the invention provides a method of administering an effective dose of iloperidone to an individual, the method comprising: determining for the individual a baseline dose of iloperidone; determining the individual's genotype at the rs1800497 single nucleotide polymorphism (SNP); and in the case that the individual's genotype at the rs1800497 SNP locus is associated with relatively greater iloperidone efficacy, administering to the individual an effective does of iloperidone that is less than the baseline dose of iloperidone.

Another aspect of the invention provides a method of treating a patient suffering a psychotic disorder, the method comprising: determining the patient's genotype at one or more of the following genetic loci: rs1800497, rs1799978, rs1799732, rs2283265, rs1076560, and rs6275; and in the case that the patient's genotype at said one or more genetic loci is associated with relatively greater iloperidone efficacy, administering to the individual an effective dose of iloperidone that is less than would otherwise be administered.

Still another aspect of the invention provides a method of treating a patient suffering a psychotic disorder, the method comprising: determining the patient's genotype at one or more of the following genetic loci: rs1800497, rs1799978, rs1799732, rs2283265, rs1076560, and rs6275; and in the case that the patient's genotype at said one or more genetic loci is associated with relatively lesser iloperidone efficacy, administering to the individual an effective dose of iloperidone that is greater than would otherwise be administered or administering to the patient a drug other than iloperidone.

BRIEF DESCRIPTION OF THE DRAWINGS

These and other features of the invention will be more readily understood from the following description of the various aspects of the invention taken in conjunction with the accompanying drawings that depict various embodiments of the invention, in which.

Figure 1:
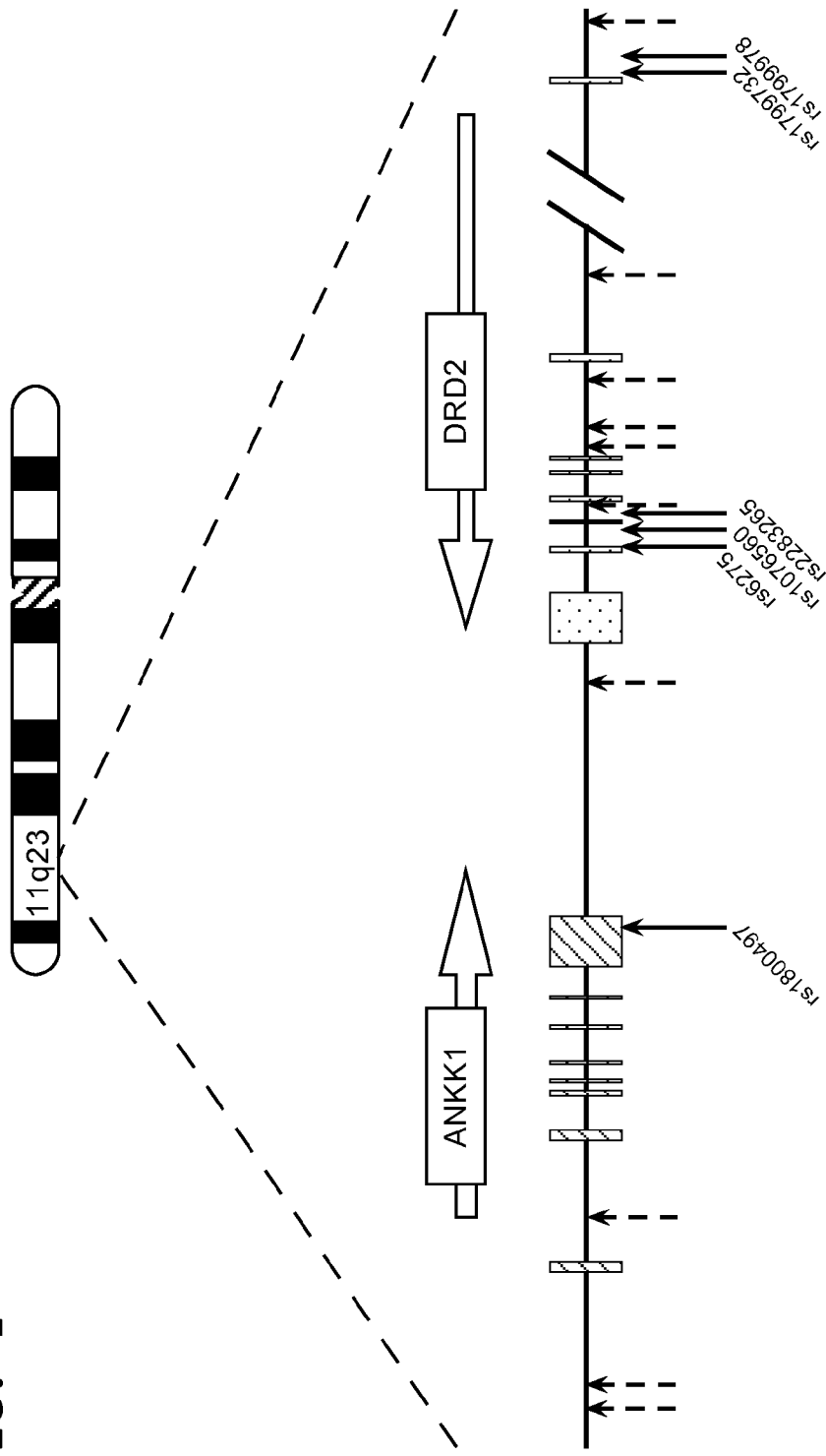
FIG. 1 shows the locations of SNPs associated with the ANKK1 and DRD2 genes.

It is noted that the drawings are not to scale and are intended to depict only typical aspects of the invention and therefore should not be considered as limiting the scope of the invention.

DETAILED DESCRIPTION OF THE INVENTION

Iloperidone (1-[4-[3-[4-(6-fluoro-1,2-benzisoxazol-3-yl)-1-piperidinyl] propoxy]-3-methoxyphenyl]ethanone) is disclosed in U.S. Pat. RE39198, which is incorporated herein by reference. Active metabolites of Iloperidone are useful in the present invention. See, e.g., WO03020707, which is incorporated herein by reference. Iloperidone metabolites include: 4-[3-[4-(6-fluoro-1,2-benzisoxazol-3-yl)-1-piperidinyl]propoxy]-3-methoxy-α-methylbenzene methanol, 1-[4-[3-[4-(6-fluoro-1,2-benzisoxazol-3-yl)-1-piperidinyl]propoxy]-3-hydroxyphenyl]ethanone, 1-[4-[3-[4-(6-fluoro-1,2-benzisoxazol-3-yl)-1-piperidinyl]propoxy]-3-methoxyphenyl]-2-hydroxyethanone, 4-[3-[4-(6-fluoro-1,2- benzisoxazol-3-yl)-1-piperidinyl]propoxy]-3-hydroxy-α-methylbenzene methanol, 4-[3-[4-(6-fluoro-1,2-benzisoxazol-3-yl)-1-piperidinyl]propoxy]-2-hydroxy-5-methoxy-α-methylbenzene methanol, 1-[4-[3-[4-(6-fluoro-1,2-benzisoxazol-3-yl)-1-piperidinyl]propoxy]-2-hydroxy-5-methoxyphenyl]ethanone, and 1-[4-[3-[4-(6-fluoro-1,2-benzisoxazol-3-yl)-1-piperidinyl]propoxy]-2,5-dihydroxyphenyl]ethanone. See, U.S. RE39198, WO93/09276 and WO95/11680, which are incorporated herein by reference.

An effective amount of iloperidone or an active metabolite thereof may be administered to a subject animal (typically a human but other animals, e.g., farm animals, pets and racing animals, can also be treated) by a number of routes. An effective amount is an amount that during the course of therapy will have a preventive or ameliorative effect on a psychotic disorder, such as schizophrenia, or a symptom thereof, or of bipolar disorder. An effective amount, quantitatively, may vary, depending upon, for example, the patient, the severity of the disorder or symptom being treated, and the route of administration.

It will be understood that the dosing protocol including the amount of iloperidone or an active metabolite thereof actually administered will be determined by a physician in the light of the relevant circumstances including, for example, the condition to be treated, the chosen route of administration, the age, weight, and response of the individual patient, and the severity of the patient's symptoms. Patients should of course be monitored for possible adverse events.

For therapeutic or prophylactic use, iloperidone or an active metabolite thereof will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

Pharmaceutical compositions useful in the practice of this invention include suitable dosage forms for oral, parenteral (including subcutaneous, intramuscular, intradermal and intravenous), transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions may be prepared by conventional techniques appropriate to the desired preparation containing appropriate amounts of iloperidone or an active metabolite thereof. See, for example, Remington's Pharmaceutical Sciences, Mack Publishing Company, Easton, Pa., 17th edition, 1985.

In making pharmaceutical compositions for use in the invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form. The term "unit dosage form" refers to physically discrete units suitable as unitary dosages for human subjects and other mammals, each unit containing a predetermined quantity of active material calculated to produce the desired prophylactic or therapeutic effect over the course of a treatment period, in association with the required pharmaceutical carrier.

Iloperidone and its active metabolites can also be formulated in a controlled release form, e.g., delayed, sustained, or pulsatile release.

Various formulations and methods of administering iloperidone and/or its derivatives have been described. For example, PCT Publication No. WO 2004/006886 A2 describes an injectable depot formulation comprising iloperidone crystals, microencapsulated depot formulations of iloperidone and a polyglycolide polylactide glucose star polymer are described in U.S. 20030091645, and methods for the administration of iloperidone directed toward, inter alia, eliminating or minimizing the prolongation of a corrected electrocardiographic QT (QTc) interval associated with increased concentrations of iloperidone or iloperidone derivatives are described in PCT Publication No. WO 2006/039663 A2, all of which are incorporated herein by reference.

Whole Genome Association Study

Several single nucleotide polymorphisms (SNPs) were found to be associated with improved response to iloperidone following a whole genome association study (WGAS) performed in a phase III clinical trial of iloperidone. The clinical trial evaluated the efficacy of iloperidone in treating patients with diagnosed schizophrenia. The study, its results, and the inferences drawn therefrom are described below.

Methods

A four-week, randomized, double-blind, placebo- and ziprasidone-controlled, multicenter inpatient phase III clinical trial of iloperidone was conducted, including 409 individuals, to assess the efficacy of iloperidone, as measured by changes in the Positive and Negative Syndrome Scale Total (PANSS-T). Six SNPs were analyzed, including two intronic SNPs and one exonic SNP, as shown in FIG. 1, as well as Table 1 below.

TABLE 1

DRD2/ANKK1 Polymorphisms Analyzed

| SNP | location |
|---|---|
| rs1799978 (−241 A/G) | upstream |
| rs1799732 (−141 C Ins/Del) | upstream |
| rs2283265 | Intron 5 |
| rs1076560 | Intron 6 |
| rs6275 (His313His) | Exon 7 |
| rs1800497 (Taq1A) | downstream |

The rs179978 SNP is believed to regulate DRD2 expression levels and striatal receptor density. Some patients carrying the -241 A allele showed a greater response when treated with risperidone than did patients carrying the -241G allele.

The rs1799732 SNP is also believed to regulate DRD2 expression levels and striatal receptor density. Schizophrenic patients carrying the -141C Del allele have been reported to take a significantly longer time to respond to antipsychotics (risperidone, olanzapine, and chlorpromazine) than patients carrying the -141C Ins allele.

Alternative splicing of exon 6 of the DRD2 gene yields at least three isoforms: short (DRD2S), long (DRD2L), and longer. The rs2283265 and rs1076560 SNPs decrease expression of DRD2S relative to DRD2L.

Schizophrenic patients with a C/C genotype for the rs6275 SNP have been reported to exhibit greater improvement when treated with clozapine, haloperidol, or risperidol than patients with a non-C/C genotype.

The rs1800497 polymorphism, originally assigned to DRD2, has since been shown to be located within exon 8 of the ankyrin repeat and kinase domain containing 1 (ANKK1) gene. The A1 allele has been linked to low striatal dopamine D2 receptor density in healthy individuals and may be associated with increased activity of the striatal L-amino acid decarboxylase, the final enzyme in the biosynthesis of dopamine. The A2 allele has been associated with schizophrenia. In some populations, A2 homozygotic patients exhibited significantly higher antipsychotic response than did heterozygotic patients. In another population, the A1 allele was shown to be in linkage disequilibrium with the minor allele of the rs2283265 and rs1076560 SNPs described above.

Patients, all diagnosed with an acute exacerbation of schizophrenia, were randomly assigned to one of three groups. A first group (n=218) received 24 mg/d (12 mg bid) of iloperidone, a second group (n=103) received 160 mg/d (80 mg bid) ziprasidone, and a third group (n=105) received a placebo. Efficacy was measured by a change from baseline in PANSS-T score.

Results

None of the six SNPs analyzed was associated with baseline PANSS-T in the general study population or in the white or black subpopulations.

Figure 2:
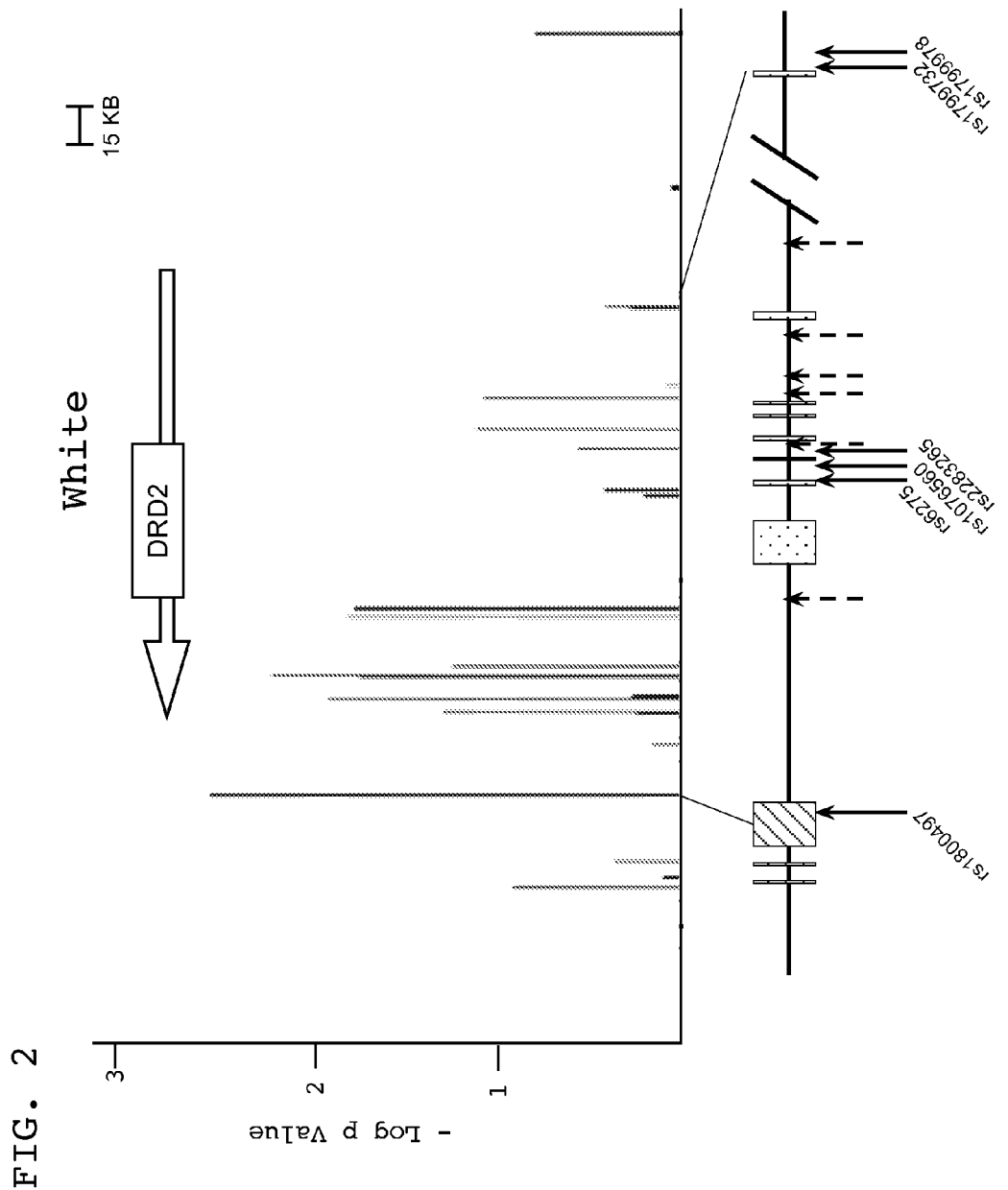
FIGS. 2 and 3 show the statistical significance of various SNPs in the white and black populations, respectively.
Figure 3:
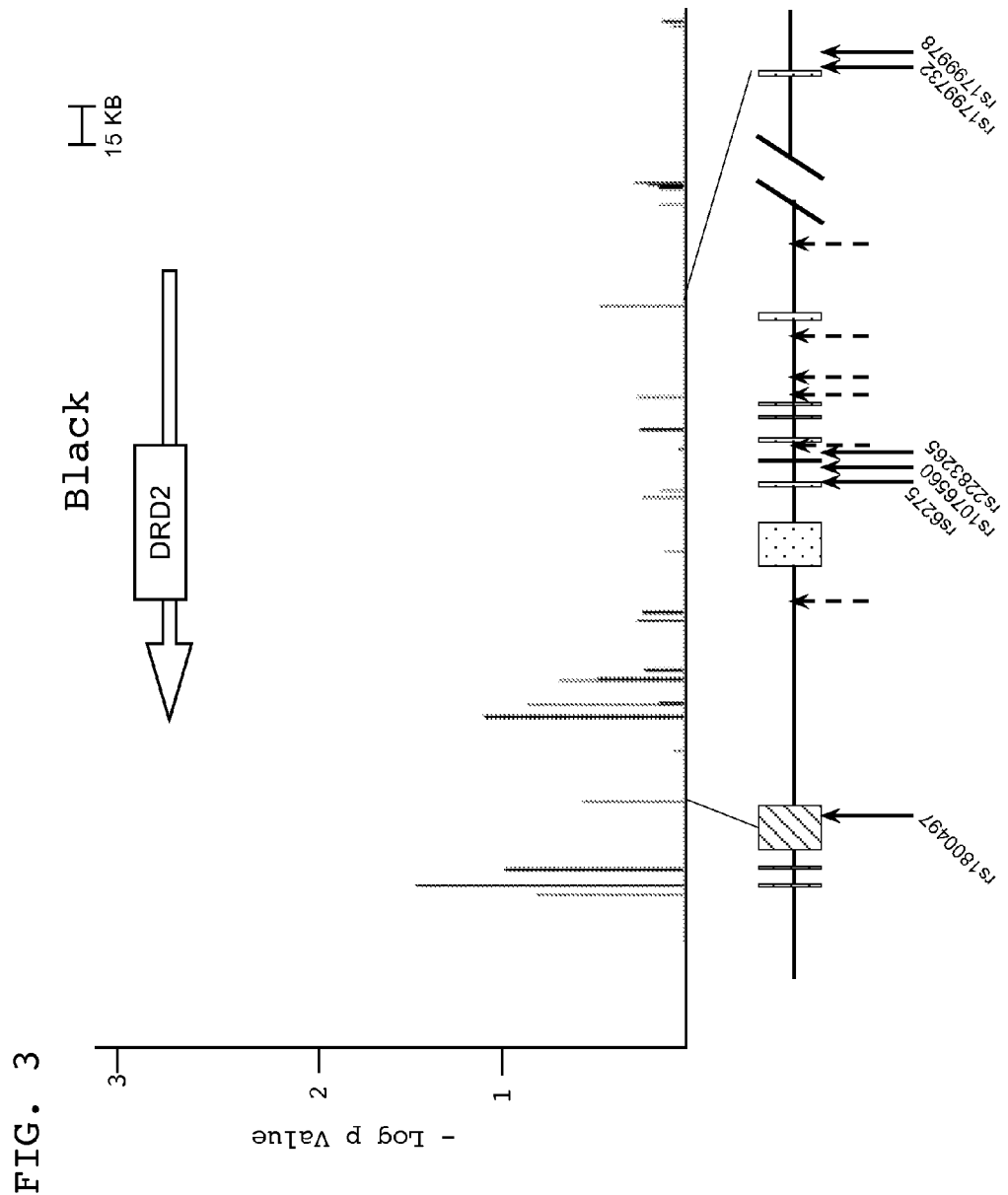
Figure 4:
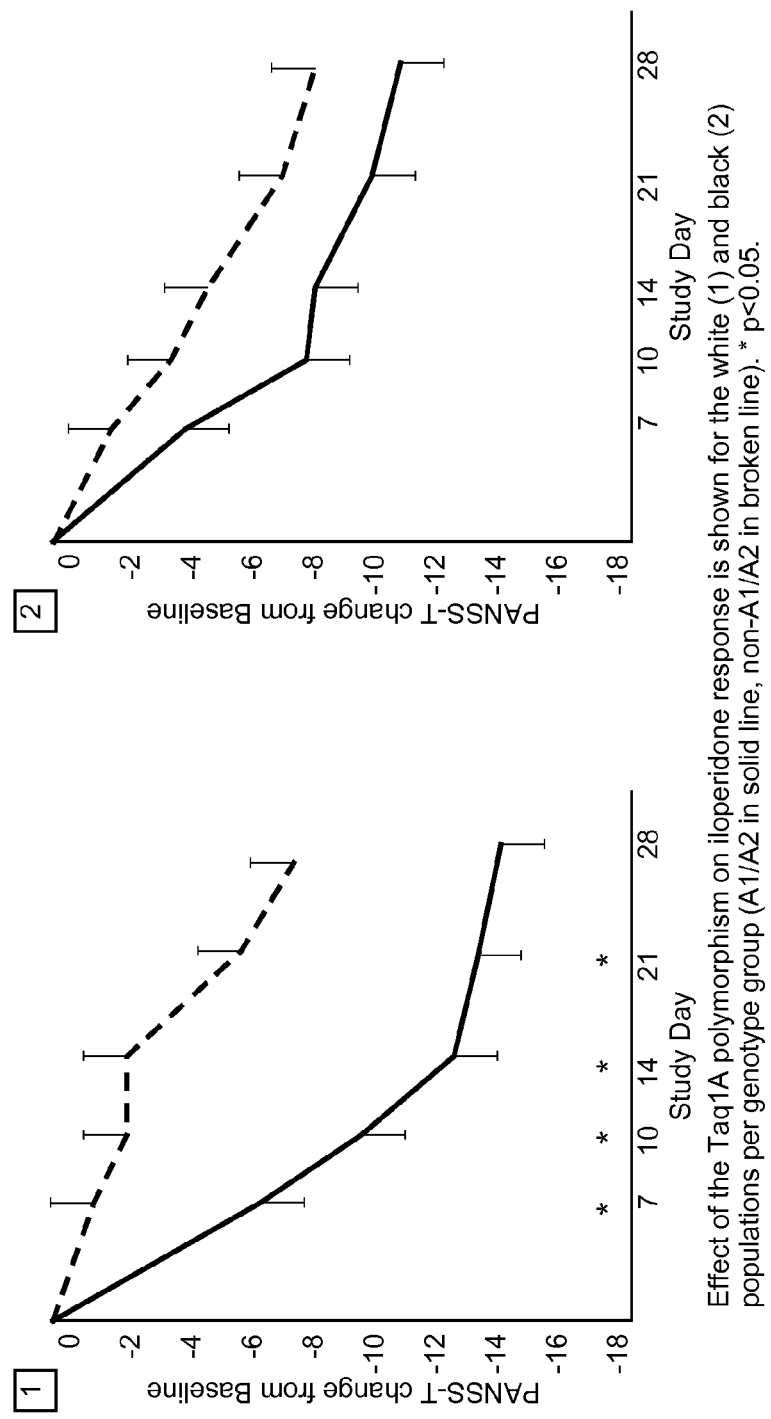
FIG. 4 shows the changes in PANSS-T based on Taq1A genotype in white and black populations.

The Taq1A polymorphism exhibited the most statistically significant effect at day 14 in the white subpopulation. See FIG. 2, cf. FIG. 3. Statistically significant effects were also observed with this SNP at days 7, 10, and 21. See FIG. 4. At day 14, the mean change in PANSS-T for non-A1/A2 patients was −12.7 (±2.1) and for A1/A2 patients was −2.1 (±2.7), resulting in a p value of 0.003.

The intronic rs2283265 and rs1076560 SNPs were also significantly associated with iloperidone response in the white subpopulation at day 14 (p=0.01 and p=0.05, respectively). White patients carrying a non-G/T genotype for rs2283265 higher efficacy (PANSS-T mean change of −11.8 (±2.0)) than white patients carrying the G/T genotype (PANSS-T mean change of −2.4 (±3.0)) (p=0.01).

It should be noted that the differences in p-values observed among the identified subpopulations (White, Black, and Asian) are not taken to suggest that the rs1800497 polymorphism is predictive of iloperidone efficacy among those groups exhibiting non-statistically significant p-values. The p-value for the overall population is statistically significant and the lack of statistically significant p-values among some subpopulations may be attributed to the sample size of the subpopulation, differences in allele frequencies, or both.

The results above may be employed in predicting the efficacy of iloperidone in the treatment of a patient based on the patient's genotype at one or more of the SNPs above.

The results may also be employed in determining an effective dose of iloperidone for a patient. For example, the recommended target dosage of iloperidone (FANAPT™) tablets is 12 to 24 mg/day administered twice daily. (The full prescribing information for FANAPT™ is hereby incorporated by reference.) This target dosage range is typically achieved by daily dosage adjustments, alerting patients to symptoms of orthostatic hypotension, starting at a dose of 1 mg twice daily, then moving to 2 mg, 4 mg, 6 mg, 8 mg, 10 mg, and 12 mg twice daily on days 2, 3, 4, 5, 6, and 7 respectively, to reach the 12 mg/day to 24 mg/day dose range. Determining whether a patient carries a genotype associated with relatively greater iloperidone efficacy, such a dosage adjustment regimen may be maintained and/or the maximum dosage may be halted at 12 mg/day (6 mg twice per day). If, on the other hand, it is determined that the patient carries a genotype associated with relatively lesser iloperidone efficacy, the dosage adjustment regimen may begin with a higher initial dosage (e.g., 2 mg/day rather than 1 mg/day) and/or the maximum dosage may be halted at 24 mg/day (12 mg twice per day). In other cases, an alternative treatment (e.g., a non-iloperidone treatment or a treatment including co-administration of iloperidone and at least one other compound) may be pursued.

These results may also be used in treating a patient suffering from a psychotic disorder, such as schizophrenia. For example, if it is determined that the patient carries a genotype associated with relatively greater iloperidone efficacy at one or more of the six SNPs described above, the patient may be administered an effective dose of iloperidone that is less than a dose that would otherwise be administered to the patient (i.e., less than a dose that would be administered to a patient not carrying a genotype associated with relatively greater iloperidone efficacy and/or less than a dose that would be administered to a patient whose genotype(s) had not been determined).

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method of determining an effective dose of iloperidone in the treatment of at least one psychotic symptom in an individual, the method comprising:

determining, or having determined, from a biological sample of the individual, the individual's genotype at the rs1800497 single nucleotide polymorphism (SNP);

in the case that the individual's genotype at the rs1800497 SNP locus is non-A1/A2:
  administering to the individual a first starting dose of iloperidone; and
  gradually increasing the dose of iloperidone administered to the individual to a first effective dose; and
in the case that the individual's genotype at the rs1800497 SNP locus is A1/A2:
  administering to the individual a second starting dose of iloperidone; and
  gradually increasing the dose of iloperidone administered to the individual to a second effective dose,
wherein the second starting dose is about twice the first starting dose and the second effective dose is about twice the first effective dose.

2. A method of administering an effective dose of iloperidone to an individual, the method comprising:
  determining, or having determined, from a biological sample of the individual, the individual's genotype at the rs1800497 single nucleotide polymorphism (SNP);
  in the case that the individual's genotype at the rs1800497 SNP is non-A1/A2, administering to the individual a first effective dose of iloperidone that is less than or equal to 12 mg/day; and
  in the case that the individual's genotype at the rs1800497 SNP is A1/A2, administering to the individual a second effective dose of iloperidone that is about twice the first effective dose.

3. The method of claim 2, wherein:
  the second effective dose of iloperidone is greater than 12 mg/day.

4. The method of claim 3, wherein the second effective dose of iloperidone is greater than or equal to 16 mg/day.

5. The method of claim 4, wherein the second effective dose of iloperidone is greater than or equal to 20 mg/day.

6. The method of claim 5, wherein the second effective dose of iloperidone is 24 mg/day.

7. The method of claim 2, further compromising:
  administering to the individual at least one other compound in combination with the second effective dose of iloperidone.

8. The method of claim 1, wherein the first effective dose is less than or equal to 12 mg/day.

9. The method of claim 1, wherein gradually increasing the dose of iloperiodone administered to the individual to the first effective dose includes:
  increasing the dose from the first starting dose of 1 mg twice daily to a first intermediate dose of 2 mg twice daily.

10. The method of claim 9, wherein gradually increasing the dose of iloperidone administered to the individual to the first effective dose further includes:
  increasing the dose from the first intermediate dose to a second intermediate dose of 4 mg twice daily.

11. The method of claim 10, wherein gradually increasing the dose of iloperidone administered to the individual to the first effective dose further includes:
  increasing the dose from the second intermediate dose to the first effective dose of 6 mg twice daily.

12. The method of claim 1, wherein gradually increasing the dose of iloperidone administered to the individual to the first effective dose includes alerting the individual to symptoms of orthostatic hypotension.

13. The method of claim 1, wherein gradually increasing the dose of iloperidone administered to the individual to the second effective dose includes alerting the individual to symptoms of orthostatic hypotension.

14. The method of claim 2, further comprising:
  alerting the individual to symptoms of orthostatic hypotension.

* * * * *